United States Patent
Danielson et al.

(10) Patent No.: US 7,341,742 B2
(45) Date of Patent: Mar. 11, 2008

(54) SIMETHICONE CONTAINING TABLET COMPOSITION AND METHOD

(75) Inventors: Douglas W. Danielson, Otsego, MI (US); Steven S. Schuehle, Allegan, MI (US); Shirish A. Shah, Kalamazoo, MI (US)

(73) Assignee: L. Perrigo Company, Allegan, MI (US)

( * ) Notice: Subject to any disclaimer, the term of this patent is extended or adjusted under 35 U.S.C. 154(b) by 976 days.

(21) Appl. No.: 10/260,882

(22) Filed: Sep. 30, 2002

(65) Prior Publication Data

US 2004/0063664 A1    Apr. 1, 2004

(51) Int. Cl.
- A61K 9/14 (2006.01)
- A61K 9/20 (2006.01)
- A61K 9/48 (2006.01)

(52) U.S. Cl. .............. 424/464; 424/451; 424/452; 424/465; 424/489

(58) Field of Classification Search ............. 424/464, 424/465, 471, 472, 489
See application file for complete search history.

(56) References Cited

U.S. PATENT DOCUMENTS

| | | | |
|---|---|---|---|
| 2,951,011 A | 8/1960 | Feinstone | |
| 3,767,794 A | 10/1973 | McVean et al. | |
| 4,127,650 A * | 11/1978 | Buehler | 514/63 |
| 4,230,693 A * | 10/1980 | Izzo et al. | 424/683 |
| 4,301,149 A * | 11/1981 | Crowley | 424/114 |
| 4,327,076 A * | 4/1982 | Puglia et al. | 424/441 |
| 4,396,604 A | 8/1983 | Mitra | |
| 4,486,412 A * | 12/1984 | Shah et al. | 424/601 |
| 5,073,384 A * | 12/1991 | Valentine et al. | 424/474 |
| 5,219,574 A * | 6/1993 | Wehling et al. | 424/464 |
| 5,401,513 A | 3/1995 | Wehling et al. | |
| 5,599,577 A * | 2/1997 | Stevens et al. | 427/2.14 |
| 6,103,260 A * | 8/2000 | Luber et al. | 424/452 |
| 2003/0091624 A1* | 5/2003 | Szymczak et al. | 424/465 |

FOREIGN PATENT DOCUMENTS

| | | | |
|---|---|---|---|
| CA | 1 042 796 | * | 11/1978 |
| CA | 1042796 | | 11/1978 |
| CA | 1 139 221 | * | 1/1983 |
| CA | 1139221 | | 1/1983 |

* cited by examiner

Primary Examiner—S. Tran
(74) Attorney, Agent, or Firm—Price, Heneveld, Cooper, DeWitt & Litton, LLP

(57) ABSTRACT

A process and pharmaceutical composition containing simethicone and magnesium carbonate allows a higher production rate of simethicone containing tablets and a more consistent end product tablet. The magnesium carbonate prevents sticking of simethicone to tablet compressing apparatuses, and may also prevent sticking of other excipients to tablet compressing apparatuses.

30 Claims, No Drawings

SIMETHICONE CONTAINING TABLET COMPOSITION AND METHOD

FIELD OF THE INVENTION

This invention relates to pharmaceutical tablets, and in particular to pharmaceutical tablets containing simethicone in a therapeutically effective amount.

BACKGROUND OF THE INVENTION

Simethicone is a liquid, oily composition. Simethicone comprises liquid methylsiloxane polymers containing a small amount of silica. Since approximately 1960, it has been used as an anti-gas and antiflatulent agent in pharmaceutical compositions. It was approved as being safe and effective for use as an anti-gas and antiflatulent by the FDA in approximately 1974. Since then, it has been widely used in a variety of pharmaceutical formulations as an anti-gas or antiflatulent agent.

In addition to being available as a liquid, simethicone has been available in powder form since approximately 1990. To create a powder, the simethicone is absorbed into maltodextrin particles, preferably agglomerated maltodextrin. (See U.S. Pat. No. 5,073,384). This so-called "granular simethicone" is especially recommended for use in tablet or other solid dosage formulations containing simethicone.

However, even powdered or granular simethicone tends to be somewhat oily to the touch, and not truly freeflowing. This causes difficulties in producing tablets or other solid dosage compositions containing simethicone.

To overcome this residual oiliness, the manufacturer of granular simethicone recommends compounding it with tribasic calcium phosphate, a well known filler/binder in directly compressible tablets. However, a known drawback of tribasic calcium phosphate is its high tendency to adhere to dies and punches. This is usually overcome by employing higher concentrations of lubricant or anti-adherent in the composition.

We have found it very difficult to compound a tablet using granular simethicone, tribasic calcium phosphate and lubricant. Tablets simply cannot be pressed fast enough. At relatively low speeds, tablets can be readily made without sticking to dies and punches. However at higher speeds, die and punch sticking becomes noticeable to an unacceptable degree. Portions of tablets will stick to the dies and punches of tablet compressing machines. During compression, the punch squeezes simethicone from the solid material. While tablets can be pressed generally successfully at slower speeds, this is not true at production speeds. On a production press (2000-3000 tablets per minute), portions of the tablet will stick to portions of the machine resulting in an end product that is inconsistent and unacceptable.

SUMMARY OF THE INVENTION

We have surprisingly found that it is possible to achieve higher production rates of granular simethicone-containing tablets by using magnesium carbonate as a processing aid. Magnesium carbonate facilitates a more consistent product quality, because portions of tablets will not stick to the dies and punches of the tablet compressing machines, and makes it unnecessary to use tricalcium phosphate or dibasic calcium. We have also found, surprisingly, that unlike many compounds which are capable of functioning as an antacid, magnesium carbonate does not adversely interfere with the effectiveness of the simethicone, even after the product has been stored for a period of time.

Another advantage of using magnesium carbonate is that the resulting tablets have greater hardness and/or structural strength than those made with a similar amount of tribasic calcium phosphate.

These and other features, advantages, and objects of the present invention will be further understood and appreciated by those skilled in the art by reference to the following specification and claims.

DETAILED DESCRIPTION OF PREFERRED EMBODIMENT

The tablet of the preferred embodiment contains a pharmaceutically effective amount of simethicone and an amount of magnesium carbonate that is effective at eliminating the sticking of simethicone and other excipients and/or actives to the dies and punches of tablet compressing machines. Preferably, the tablet is substantially free of either tricalcium phosphate or dicalcium phosphate. Simethicone may be administered to humans in a daily dosage regimen of up to 500 mg/day. The range of simethicone contained in each tablet is preferably from about 20 mg to about 250 mg, while the more preferred amount of simethicone per tablet is about 40 mg to about 125 mg. The weight ratio of magnesium carbonate to simethicone preferably falls with in the range of from about 90:125 to about 115:125. The total tablet weight may be from about 500 mg to about 1500 mg, and the preferred total tablet weight is from about 750 mg to about 1000 mg.

In order for a compound to be successful as an oil absorbent for simethicone it must do three things: 1) it must promote the tablet forming characteristics of the simethicone containing granulation; 2) it must not interfere with the effectiveness of the simethicone as demonstrated by the U.S.P. simethicone foam break test; and 3) there are several agents which satisfy 2) in fresh tablets but the agent must continue to satisfy condition #2 for the life of the product.

As indicated in U.S. Pat. No. 4,396,604, compounds which act as antacids interfere, over time, with the effectiveness of simethicone. While magnesium carbonate has previously been used with simethicone as an antacid ingredient, it has not heretofore been used with granular simethicone as an absorbent processing aid. Nor has it been recognized that magnesium carbonate, unlike other antacid materials, does not significantly interfere with the effectiveness of simethicone, even over time. For example, the defoaming activity of simethicone in an antidiarrheal/simethicone containing chewable tablet in an accelerated stability test at 40° C. and at 75% relative humidity yields results of an 11 second defoaming activity at 1 month, a 12 second defoaming activity at 2 months and a 10 second defoaming activity at 3 months. A further example of the same accelerated stability test using the same simethicone containing tablets with a temperature of 25° C. and a relative humidity at 60% yields defoaming activity of the simethicone at 3 months of 10 seconds and at 6 months a defoaming activity of 11 seconds.

Various pharmaceutical actives and tablet excipients may also be combined into the tablet mixture, prior to compression, such as by using rotating shell blenders. Examples of such blenders include double-cone and twin shell blenders.

Examples of types of tablet excipients include, but are not limited to, fillers, binders, diluents, processing aids, e.g. glidants, granulating agents, etc. Specific examples include, without limitation, microcrystalline cellulose, lactose, starch, pregelatinized starch, sucrose, dextrose, corn syrup solids, stearic acid, magnesium stearate, etc.

Preferably, the tablet is substantially free of tricalcium phosphate or dicalcium phosphate. The term "substantially free" is intended to allow for the presence of some dicalcium phosphate or tricalcium phosphate, but not in an amount sufficient to cause production problems such as material sticking to the tablet press dies and punches.

Other pharmaceutical actives may also be incorporated into the tablet. Examples of such pharmaceutical actives include, but are not limited to antidiarrheals, such as attapulgite, loperamide hydrochloride, diphenoxylate hydrochloride, polycarbophil and activated charcoal; and antacids, such as aluminum hydroxide, bismuth subcarbonate, magnesium carbonate-aluminum hydroxide coprecipitate, sodium bicarbonate, sodium citrate, calcium carbonate, magnesium trisilicate and magnesium hydroxide.

The preferred form of magnesium carbonate is as an impalpable powder. An impalpable powder is a powder that is so finely divided that no grains or grit can be felt by touch. An advantage of using magnesium carbonate as a processing aid is that magnesium carbonate is an efficient absorbent. Less amounts of magnesium carbonate may be used as an absorbent, than amounts of conventional absorbing agents, allowing a smaller, more desirable tablet size. Additionally, as a finely divided powder, the magnesium carbonate will thus have the greater coating/drying properties per unit weight than it would as a coarse powder. The particle size range of the magnesium carbonate is from about 1 microns to about 34 microns. The surface area range of the magnesium carbonate particles is from about 3 to about 80 $m^2$/gram, more preferably the surface area range of the magnesium carbonate particles is about 40.5 $m^2$/g.

The preferred form of simethicone is the so-called granular simethicone, where simethicone is absorbed onto or into a carrier, preferably maltodextrin. The term granular simethicone as used herein is intended to encompass not only simethicone adsorbed onto maltodextrin, but also simethicone adsorbed onto or into solid carriers, where the resulting granules are, like simethicone adsorbed onto maltodextrin, still oily to the touch. Granular simethicone is available at 30% and 40% simethicone levels.

A preferred form of granular simethicone is a mixture of simethicone and maltodextrin that is agglomerated to form a uniform, poorly flowing, granular combinate containing from about 10 to about 50 percent simethicone and 90 to about 50 percent maltodextrin by weight, and more preferably from about 20 to about 40 percent simethicone and from about 80 to 60 percent maltodextrin by weight.

Granular simethicone per se is neither free flowing nor compressible into tablets. The use of magnesium carbonate in combination with granular simethicone makes granular simethicone both free flowing and readily compressible into tablets.

The granular-simethicone and the magnesium carbonate may be blended in a twin shell blender to yield a gross/coarse mixing of the granular simethicone with the magnesium carbonate. Preferably, the coarse mixture is then cycled through an oscillating granulator, whereby the surface oil on the maltodextrin may be adequately adsorbed by the magnesium carbonate. The ratio of magnesium carbonate to simethicone in the granular simethicone is preferably selected to allow excess oil on the surface of the simethicone granules to be adsorbed onto the magnesium carbonate to overcome the poor flow and poor compressibility properties of the granular simethicone. A suitable weight ratio of magnesium carbonate to the simethicone in the granular simethicone is from about 90:125 to about 115:125. Although higher amounts of magnesium carbonate could be used, there is no reason to do so for processing purposes, once the excess oil has been adequately adsorbed. However, one might do so for other reasons.

In the foregoing description, it will be readily appreciated by those skilled in the art that modifications may be made to the invention without departing from the concepts disclosed herein. Such modifications are to be considered as included in the following claims, unless these claims by their language expressly state otherwise.

EXAMPLES

The following examples show that magnesium carbonate is useful as an absorbent for simethicone in pharmaceutical dosage forms which do not contain substantial amounts of either tricalcium phosphate or dicalcium phosphate, and provides good flow properties, good friability and tablet hardness and no sticking to tablet compression machine components. Unless otherwise stated, the "simethicone mix" used in the Examples refers to a composition as follows:

| Description | Quantity |
|---|---|
| Dextrose Monohydrate, USP | 25.0 kg |
| Yellow #10 D&C Dye Lake | 250 gm |
| Blue #1 FD&C Dye Lake | 90.0 gm |
| Simethicone Pwd GS (30%) | 417 kg |
| Magnesium Carbonate | 100 kg |
| Microcryst Cellulose | 200 kg |
| Dextrates | 275 kg |
| Stearic Acid | 8.00 kg |
| Total Quantity | 1025 kg |

The simethicone mix is processed by pre-blending magnesium carbonate and simethicone powder GS 30% in a V-blender. This pre-blended mix is then dry granulated and placed in a V-shell blender. Dextrates and microcrystalline cellulose are then added to the pre-blended mix in the V-shell blender and the pre-blended mix, dextrates and microcrystalline cellulose are blended for approximately 10 minutes. Blue #1 FD&C dye lake, yellow #10 D&C dye lake and dextrose are combined in a drum roller, dry granulated and then placed in the V-shell blender with the pre-blended mix, dextrates and microcrystalline cellulose. An additional amount of dextrose is dry granulated in the same granulator that the colorants were granulated in, for the purpose of rinsing the granulator after the dry granulation of the colorants. This amount of dextrose is also added to the V-shell blender. An amount of stearic acid is then passed through a 30 mesh screen and added to the V-shell blender. The pre-blended mix, dextrates, microcrystalline cellulose, colorants, dextrose and stearic acid are then blended in the V-shell blender for 3 minutes. A sample of the V-shell blender mix is then measured to test blend uniformity. Upon meeting satisfactory blend uniformity requirements, the simethicone layer mix is transferred to tote bins.

Comparative Examples 1-3

The following examples are given to illustrate the specific problems of using substantial amounts of dicalcium or tricalcium phosphate in a simethicone containing tablet.

Example 1

| Materials | |
|---|---|
| Simethicone mix | 21.5 kg |
| Tricalcium Phosphate | 573 g |
| Microcrystalline Cellulose | 1433 g |

Approximately 21.5 kg of the simethicone mix and 573 g of the tricalcium phosphate were passed through a 16 mesh screen into a 5 cubic foot rotating shell blender. Approximately 1433 g of microcrystalline cellulose was then added to the blender and the components were blended for 10 minutes. This blended mixture was then compressed into tablets containing 125 mg of simethicone. Sticking problems on the tablet machine dies and punches occurred during this tablet compression.

Example 2

| Materials | |
|---|---|
| Simethicone mix | 40.0 kg |
| Tricalcium phosphate | 2.13 kg |
| Microcrystalline cellulose | 5.33 kg |

Approximately 40.0 kg of the simethicone mix and 2.13 kg of the tricalcium phosphate were passed through a 16 mesh screen into a 5 cubic foot rotating shell blender. The simethicone and tricalcium phosphate were blended for 10 minutes. Approximately 5.33 kg of microcrystalline cellulose was then added to rotating shell blender and the components were blended for 5 minutes. This blended mixture was then compressed into tablets containing 125 mg of simethicone. This mixture resulted in tablets that capped severly during tablet compression.

Example 3

The object of this example was to determine if the addition of 100 mg microcrystalline cellulose per tablet would remedy the sticking problem seen with the compression of the simethicone layer.

| Materials | |
|---|---|
| Simethicone mix | 15 kg |
| Dibasic calcium phosphate | 1700 g |
| Microcrystalline cellulose | 2000 g |
| Magnesium stearate | 100 g |

A portion of the simethicone mix, approximately 1700 g of dibasic calcium phosphate and a portion of microcrystalline cellulose were combined in a 5 cubic foot twin shell blender and blended for 5 minutes. A portion of microcrystalline cellulose and a portion of the simethicone layer mix were passed through a 16 mesh screen and then added to the blend. The blender was then run for 3 minutes. This blended mixture was then compressed into tablets containing 125 mg of simethicone using a Beta press. Increasing the amount of dibasic calcium phosphate by 85 mg per tablet and increasing the amount of microcrystalline cellulose by 100 mg per tablet did not prevent sticking.

Preferred Embodiment Examples 4-7

Example 4

The following examples are given to more precisely and particularly illustrate the specific details of the present invention. Equivalent procedures and quantities will occur to those skilled in the art and therefore the following examples are not meant to define the limits of the present invention, these being defined by the scope of the appended claims. The object of this example was to evaluate magnesium carbonate as an "oil adsorbing aid/flow agent" for granular simethicone.

| Materials | |
|---|---|
| Granular simethicone (30%) | 4170 g |
| Magnesium carbonate | 1000 g |
| Microcrystalline cellulose | 4827 g |

Approximately 4170 g of granular simethicone and 1000 g of magnesium carbonate were blended and passed through a 10 mesh screen into a 16 quart twin shell blender. The mixture was blended for 15 minutes. Approximately 4827 g of microcrystalline cellulose was blended with the granular simethicone and magnesium carbonate mixture creating a new mixture. This resulted in the determination that magnesium carbonate worked well as an oil adsorbing agent/flow aid for granular simethicone because there was no sticking. The blend was compressed into tablets containing 125 mg simethicone each. Friability tests were run to determine the brittleness of the tablets. The friability tests determined the tablets as having 0.2% friability. Hardness test were also run to determine hardness of the tablets. The hardness tests results were as follows:

| Hardness: | 6.0 scu | 6.5 scu |
|---|---|---|
| | 5.9 | 6.8 |
| | 5.4 | 5.6 |
| | 5.3 | 6.4 |
| | 5.5 | 4.9 |

Example 5

In example 5 the simethicone mixture was compressed into bi-layered tablets on a bi-layered tablet press, with the simethicone in one layer of the tablet, and the anti-diarrheal loperamide contained in the second layer.

The second layer in each example is made by first granulating loperamide HCl with sodium starch glycolate, dextrates, microcrystalline cellulose and starch 78-1551. The loperamide HCl granules are then combined with mannitol and sodium starch glycolate, aspartame, dyes and flavorants. An amount of the loperamide layer mix is combined with an amount of the simethicone layer mix in a bi-layered tablet press so that the loperamide layer mix comprises 600 gm of the bi-layered tablet and the simethicone layer mix comprises 1025 gm of the bi-layered tablet. The loperamide layer mix and the simethicone layer mix are then compressed to form a bi-layered tablet having 2 mg of loperamide HCl and 125 mg of simethicone.

| Materials | |
|---|---|
| Granular simethicone (30%) | 20.85 kg |
| Directly compressible sugar | 14.99 kg |
| Microcrystalline cellulose | 7.50 kg |
| Magnesium carbonate | 5.00 kg |
| Stearic acid | 400 g |
| D&C yellow #10 dye lake | 10 g |
| FD&C blue #1 dye lake | 3.75 g |

Approximately 20.85 kg of granular simethicone and 5.00 kg of magnesium carbonate were combined in a 5 cubic foot twin shell blender and blended for 20 minutes. This resulted in a dry blend that was free flowing. This blend was then dry granulated and passed through a 0.125 inch drilled-hole screen back into a 5 cubic foot blender. Approximately 3.75 g of FD&C blue #1 dye lake, 10 g of D&C yellow #10 dye lake and 1 kg of microcrystalline cellulose were blended and passed through a 16 mesh screen into the same 5 cubic foot blender that contained the simethicone blend. The remainder of the microcrystalline cellulose, approximately 6.50 kg, was then added to the blender. Also, approximately 14.99 kg of directly compressible sugar was added to the blender at this time. The blender was then run for 15 minutes. Approximately 400 g of stearic acid was passed through a 30 mesh screen into the blender and was blended for 3 minutes. The blend was compressed into tablets containing 125 mg of simethicone. Sticking and capping of the blend to the tablet compressing machines did not occur. Each trial represents measurements and observations at 10-15 minutes intervals during the compression of the tablets.

| Trial #1 | | | |
|---|---|---|---|
| | Weight (gm) | Hardness (scu) | Thickness (inches) |
| | 1.536 | 8.9 | 0.237 |
| | 1.480 | 6.6 | 0.240 |
| | 1.527 | 7.9 | 0.241 |
| | 1.519 | 9.5 | 0.237 |
| | 1.530 | 8.5 | 0.238 |
| Avg. | 1.519 | | |

Comment: No punch sticking after 10 minutes of press running time.

| Trial #2 | | | |
|---|---|---|---|
| | Weight (gm) | Hardness (scu) | Thickness inches |
| | 1.532 | 8.8 | 0.239 |
| | 1.541 | 8.6 | 0.227 |
| | 1.537 | 9.1 | 0.239 |
| | 1.545 | 8.2 | 0.235 |
| | 1.529 | 8.0 | 0.240 |
| Avg. | 1.531 | | |

Comment: No sticking after 20 minutes of total press running time.

| Trial #3 | | |
|---|---|---|
| Weight (gm) | Hardness (scu) | Thickness (inches) |
| 1.540 | 9.4 | 0.239 |
| 1.537 | 5.6 | 0.226 |

-continued

| Trial #3 | | |
|---|---|---|
| Weight (gm) | Hardness (scu) | Thickness (inches) |
| 1.473 | 7.5 | 0.241 |
| 1.534 | 7.3 | 0.237 |
| 1.525 | 8.9 | 0.237 |
| Avg. 1.514 | | |

Comment: No sticking after 30 minutes of total press running time.

| Trial #4 | | |
|---|---|---|
| Weight (gm) | Hardness (scu) | Thickness (inches) |
| 1.521 | 9.1 | 0.240 |
| 1.542 | 8.9 | 0.241 |
| 1.527 | 7.9 | 0.242 |
| 1.511 | 8.8 | 0.239 |
| 1.522 | 7.7 | 0.241 |

Comment: No sticking after 40 minutes of total press running time.

| Trial #5 | |
|---|---|
| Hardness (scu) | Thickness (inches) |
| 9.8 | 0.240 |
| 8.5 | 0.238 |
| 7.6 | 0.241 |
| 8.3 | 0.241 |
| 5.1 | 0.220 |
| Avg. 1.341 | |

Comment: No sticking after 50 minutes of total press running time.

| Trial #6 | | |
|---|---|---|
| Weight (gm) | Hardness (scu) | Thickness (inches) |
| 1.55 | 9.2 | 0.240 |
| 1.54 | 7.9 | 0.239 |
| 1.54 | 9.2 | 0.239 |
| 1.56 | 8.6 | 0.240 |
| 1.53 | 9.6 | 0.238 |
| Avg. 1.527 | | |

Action: Increased RPM to 30 rpm run for 10 minutes and collected tablets.
Comment: No sticking after 60 minutes of total press running time.

| Trial #7 | | |
|---|---|---|
| Weight (gm) | Hardness (scu) | Thickness (inches) |
| 1.530 | 8.0 | 0.242 |
| 1.546 | 7.7 | 0.243 |
| 1.535 | 6.9 | 0.244 |
| 1.540 | 10.2 | 0.240 |
| 1.513 | 8.8 | 0.236 |
| Avg. 1.538 | | |

Action: Run at 30 rpm for 20 minutes.
Comment: No capping after 70 minutes of total press running time.

Example 6

In this example Emdex (dextrates) were used rather than dextrose to make the simethicone mix.

| Materials | |
|---|---|
| Granular simethicone (30%) | 2842 g |
| Dextrates, Emdex | 2051 g |
| Microcrystalline Cellulose | 1365 g |
| Magnesium Carbonate | 682.5 g |
| Stearic acid | 56.0 g |
| D&C yellow #10 dye lake | 1.365 g |
| FD&C blue #1 dye lake | 0.511 g |

Approximately 2842 g of granular simethicone and 682.5 g of magnesium carbonate were blended for 15 minutes in a 16 quart twin shell blender. The simethicone mixture was then dry granulated and passed through a 0.125 inch screen and placed back into the blender. Approximately 1365 g of microcrystalline cellulose was added to the blender. Approximately 2051 g of Emdex was passed through a 10 mesh screen and placed in the blender. The simethicone, microcrystalline cellulose and Emdex combination was blended for 10 minutes. Approximately 56 g of stearic acid was passed through a 30 mesh screen and added to the simethicone mixture. Approximately 1.365 g of D&C yellow #10 dye lake, 0.511 g FD&C blue #1 dye lake and Emdex were passed through a 30 mesh screen and then combined with the simethicone mixture creating a new mixture. This new simethicone mixture was blended for approximately 3 minutes. The blend was compressed into tablets containing 125 mg of simethicone each.

Friability tests were run which resulted in the tablets having 0.3% friability. Additionally, the following test were run resulting in the data provided below:

| Hardness: | 4.1 scu | 4.2 scu |
|---|---|---|
| | 4.4 | 4.0 |
| | 4.4 | 3.9 |
| | 3.9 | 4.3 |
| | 4.0 | 3.9 |
| Individual weight: | 1.012 g | 1.022 g |
| | 1.026 | 1.037 |
| | 1.022 | 1.018 |
| | 1.020 | 1.022 |
| | 1.036 | 1.021 |
| Thickness: | 0.171 inches | |
| | 0.170 | |
| | 0.168 | |
| | 0.165 | |

The thickness of the bi-layered tablet measured approximately 0.241 inches which is about 0.01 inches thinner than the tablet of the dextrose formula. The simethicone foam break time was approximately 2 seconds. Tablets made with Emdex (dextrates) are approximately 1 scu harder, less friable and thinner than the tablets of the dextrose formula. Also, the granulation is freer flowing.

Example 7

In Example 7, the simethicone layer mix from Example 6 was compressed into bilayered tablets with the loperamide layer mix from Example 5. Each trial represents measurements made at approximately 10-15 minute intervals.

| Trial #1 | | |
|---|---|---|
| Weight (gm) | Hardness (scu) | Thickness (inches) |
| 1.628 | 11.1 | 0.255 |
| 1.626 | 11.1 | 0.254 |
| 1.624 | 9.7 | 0.255 |
| 1.624 | 9.9 | 0.255 |
| 1.630 | 10.0 | 0.255 |
| Avg. 1.624 | | |

Action: run-off batch
Comment: Initial Measurements

| Trial #2 | | |
|---|---|---|
| Weight (gm) | Hardness (scu) | Thickness (inches) |
| 1.620 | 10.4 | 0.251 |
| 1.622 | 11.1 | 0.253 |
| 1.633 | 12.1 | 0.253 |
| 1.635 | 10.8 | 0.255 |
| 1.615 | 9.7 | 0.255 |
| Avg. 1.625 | | |

Comment: Measurements after approximately 10 minutes press running time.

| Trial #3 | | |
|---|---|---|
| Weight (gm) | Hardness (scu) | Thickness (inches) |
| 1.625 1.617 | 10.2 | 0.228 |
| 1.624 1.604 | 10.2 | 0.253 |
| 1.616 1.614 | 10.8 | 0.255 |
| 1.605 1.625 | 10.3 | 0.253 |
| 1.611 1.615 | 10.2 | 0.232 |
| Avg. 1.616 | | |

Comment: Measurements after approximately 20 minutes total press running time.

| Trial #4 | | |
|---|---|---|
| Weight (gm) | Hardness (scu) | Thickness (inches) |
| 1.608 | 11.1 | 0.250 |
| 1.606 | 10.1 | 0.251 |
| 1.612 | 10.5 | 0.250 |
| 1.628 | 10.5 | 0.252 |
| 1.620 | 10.9 | 0.252 |
| Avg. 1.614 | | |

Comment: Measurements after approximately 30 minutes total press running time.

| Trial #5 | | |
|---|---|---|
| Weight (gm) | Hardness (scu) | Thickness (inches) |
| 1.633 | 11.9 | 0.259 |
| 1.645 | 11.4 | 0.254 |
| 1.624 | 11.8 | 0.256 |

-continued

Trial #5

| Weight (gm) | Hardness (scu) | Thickness (inches) |
|---|---|---|
| 1.630 | 11.8 | 0.252 |
| 1.634 | 10.5 | 0.253 |
| Avg. 1.630 | | |

Comment: Measurements after approximately 40 minutes total press running time.

Trial #6

| Weight (gm) | Hardness (scu) | Thickness (inches) |
|---|---|---|
| 1.603 1.602 | 9.6 | 0.250 |
| 1.613 1.608 | 11.0 | 0.258 |
| 1.602 1.600 | 10.2 | 0.255 |
| 1.605 1.613 | 10.8 | 0.254 |
| 1.611 | 11.5 | 0.251 |

Comment: Measurements after approximately 50 minutes total press running time.

Trial #7

| Weight (gm) | Hardness (scu) | Thickness (inches) |
|---|---|---|
| 1.638 1.641 | 12.9 | 0.256 |
| 1.627 1.625 | 12.4 | 0.253 |
| 1.624 1.636 | 12.3 | 0.260 |
| 1.636 1.622 | 13.3 | 0.253 |
| 1.607 1.644 | 12.6 | 0.255 |

Comment: Measurements after approximately 60 minutes total press running time.

Trial #8

| Weight (gm) | Hardness (scu) | Thickness (inches) |
|---|---|---|
| 1.633 | 11.4 | 0.252 |
| 1.622 | 11.8 | 0.255 |
| 1.625 | 12.8 | 0.255 |
| 1.629 | 12.3 | 0.253 |
| 1.614 | 12.0 | 0.254 |

Comment: Measurements after approximately 70 minutes total press running time.

Trial #9

| Weight (gm) | Hardness (scu) |
|---|---|
| 1.632, 1.625 | 12.3 |
| 1.615, 1.621 | 13.1 |
| 1.635, 1.617 | 12.2 |
| 1.629, 1.620 | 12.4 |
| 1.638, 1.641 | 13.4 |
| Avg. 1.629 | |

Comment: Measurements after approximately 80 minutes total press running time.
Friability: 4 minutes
Initial weight: 16.398 gm
Final weight: 16.181 gm
1.3% friability This resulted in well compressed tablets that were hard and of low friability. Sticking of the materials to the press did not occur with this formulation.

The invention claimed is:

1. A pharmaceutical composition comprising granular simethicone blended with a processing aid amount of magnesium carbonate in which the ratio of the magnesium carbonate to simethicone contained in the granular simethicone is from about 90:125 to about 115:125.

2. The composition of claim 1 wherein:
the magnesium carbonate is in an impalpable powder form.

3. The composition of claim 2, wherein:
the magnesium carbonate particle size is from about 1 micron to about 34 microns.

4. The composition of claim 2, wherein:
the magnesium carbonate particle surface area is from about 3 $m^2$/gram to about 80 $m^2$/gram.

5. The composition of claim 1 wherein:
the magnesium carbonate is in an impalpable powder form.

6. The composition of claim 1, further comprising at least one additional pharmaceutical active other than simethicone.

7. The composition of claim 1, further comprising at least one antidiarrheal pharmaceutical active.

8. The composition of claim 1, further comprising at least one antacid pharmaceutical active.

9. The composition of claim 1, further comprising:
at least one additional pharmaceutical excipient other than magnesium carbonate.

10. The pharmaceutical composition of claim 1, which is substantially free of tricalcium phosphate and dicalcium phosphate.

11. A compressed pharmaceutical tablet comprising from about 1 mg to 500 mg of simethicone absorbed onto or into a carrier, and an amount of magnesium carbonate that is effective to prevent simethicone from sticking to a punch or die during compression of the tablet, wherein the tablet contains magnesium carbonate and simethicone in a ratio of from about 90 to 115 parts by weight of magnesium carbonate to about 125 parts by weight simethicone.

12. The tablet of claim 11, wherein the tablet contains from about 40 mg to about 125 mg of simethicone.

13. The tablet of claim 12, wherein the magnesium carbonate is in an impalpable form.

14. The composition of claim 13, wherein:
the magnesium carbonate particle size is from about 1 micron to about 34 microns.

15. The composition of claim 13, wherein:
the magnesium carbonate particle surface area is from about 3 $m^2$/gram to about 80 $m^2$/gram.

16. The tablet of claim 11, wherein the magnesium carbonate is in an impalpable form.

17. The tablet of claim 11, further comprising at least one additional pharmaceutical active other than simethicone.

18. The tablet of claim 17, further comprising at least one antidiarrheal pharmaceutical active.

19. The tablet of claim 11, in which the simethicone and carrier combination comprises 30-40% by weight simethicone, and the tablet contains about one part magnesium carbonate to about 4 parts granular simethicone.

20. The tablet of claim 19, which also includes microcrystalline cellulose, dextrates, dextrose and a processing aid.

21. The tablet of claim 11, further comprising at least one pharmaceutical excipient other than magnesium carbonate.

22. The pharmaceutical composition of claim 11, which is substantially free of tricalcium phosphate and dicalcium phosphate.

23. A multi-part tablet comprising:
a first part comprising granular simethicone, magnesium carbonate and at least one other excipient; and a second part comprising another pharmaceutical active and at least one other excipient.

24. The tablet of claim 23, in which the simethicone and carrier combination comprises 30-40% by weight simethicone, and said first part contains about one part magnesium carbonate to about 4 parts granular simethicone.

25. The tablet of claim 24, in which said first part also includes microcrystalline cellulose, dextrates, dextrose and a processing aid.

26. The tablet of claim 23, in which said other pharmaceutical active in said second part is an anti-diarrheal agent.

27. The tablet of claim 26, in which said anti-diarrheal agent is loperamide and pharmaceutically acceptable salts thereof.

28. The tablet of claim 27, in which said loperamide or a pharmaceutically acceptable salt is granulated with granulating excipients, and said second part comprises excipients blended with said granulated loperamide or pharmaceutically acceptable salts.

29. The tablet of claim 26, in which said anti-diarrheal agent is granulated with granulating excipients, and said second part comprises excipients blended with said granulated anti-diarrheal agent.

30. The pharmaceutical composition of claim 23, which is substantially free of tricalcium phosphate and dicalcium phosphate.

* * * * *